United States Patent [19]

Mercer

[11] 3,952,103

[45] Apr. 20, 1976

[54] HERPES VIRAL INFECTION TREATMENT

[76] Inventor: James B. Mercer, 13109 W. 95th St., Lenexa, Kans. 66215

[22] Filed: Oct. 15, 1974

[21] Appl. No.: 514,798

Related U.S. Application Data

[63] Continuation-in-part of Ser. No. 370,952, June 18, 1973, Pat. No. 3,856,966.

[52] U.S. Cl. .............................................. 424/273
[51] Int. Cl.² ...................................... A61K 31/415
[58] Field of Search ................................... 424/273

[56] References Cited
OTHER PUBLICATIONS

The Merck Manual, 12 Ed., 1972, Merck & Co., Inc. Rahway, N.J., pp. 18t–21t.

*Primary Examiner*—Jerome D. Goldberg
*Attorney, Agent, or Firm*—Fishburn, Gold & Litman

[57] ABSTRACT

The administration internally to humans of 1-(β-hydroxethyl)-2-methyl-5-nitromidazole, (metronidazole) in a dosage range for adult humans of about 31 to 1,000 mgs per twenty-four hour period, is an effective therapeutic treatment certain of viral infections.

4 Claims, No Drawings

HERPES VIRAL INFECTION TREATMENT

This is a continuation-in-part of Application Ser. No. 370,952 filed June 18, 1973 entitled TREATMENT OF VIRAL INFECTIONS, now U.S. Pat. No. 3,856,966.

The invention herein described relates to a method of treating certain viral infections in humans, such as herpes hominus, herpes zoster, herpes simplex and herpes virus associated mononeucleosis.

The objects of this invention are: to provide a method for systematically treating certain viral infections in humans; to provide such a treatment which is effective in combating herpes viral infection selected from the group consisting of zoster, simplex, hominus and mononeucleosis; to provide such a method that is suitable for intensive therapy as well as long-term maintenance and intermittent therapy; and to provide such a treatment which is easily administered and usually well tolerated by the receipient.

1-$\beta$-hydroxyethyl)-2-methyl-5-nitromidazole, (metronidazole) is a known alkylating agent of relatively low toxicity in mammals which is thought to interfere with nucleic acid biosynthesis. It appears that metronidazole can penetrate all tissues of the body quite readily and its effectiveness, in the treatment of viral infections, is believed to relate to blockage or interference with the viral matabolism cycle necessary for cell infection. The agent apparently suppresses virus production while natural body defenses function to eliminate viral material from the system. Metronidazole is readily absorbable from the human intestinal tract and may be administered orally as well as by vaginal or rectal inserts, as indicated.

Clinical observations upon the administration of metronidazole in the treatment of viral infections have demonstrated marked patient improvement and in many cases, apparent complete remissions.

A typical intense treatment for an average size human adult patient comprises 250 mgs of the agent four times daily for a period of about four weeks, then a reduction to 125 mgs four times daily for several additional weeks and thereafter further reduction, depending upon the tolerance of the patient and absence of symptoms. Doses for children are proportionally less according to body weight.

An ultimate effective long-term maintenance dose was found to be as low as 31 mgs per day. The most common effective maintenance dose has been determined to be about 125 mgs per day for a substantial percentage of patients, with 250 mgs per day being indicated and well tolerated for other patients, depending on age, size, and physical condition. A reasonable maximum dosage for adult humans appears to be about 1,000 mgs per day. Renewal of treatment has been found to be effective upon a return of symptoms after treatment was discontinued.

Regarding side effects, some persons were found to experience nausea but it generally disappeared after a few weeks. In rare instances there was a slight soreness of the mouth or a white tongue indicating need for dosage reduction. Some dizziness and dryness of the mouth and vagina were occasionally noted and a few persons complained of a bad taste. Also, moderate leukopenia was occasionally observed, which normally returned to normal after dosage reduction, completion of a treatment regimen or as therapy continued.

Metronidazole is believed contraindicated in patients under treatment with desulfadram (Antabuse) and in uncompensated hypothyroid patients. Because metronidazole appears to cross the placental barrier and enter the fetal circulation rapidly and further since its effect on fetal development are not definitely known, it is also thought to be contrindicated during the first trimester of pregnancy, except when a history of prior existing viral infection may endanger that pregnancy.

The initial neurological signs of metronidazole overdose in humans appear to be increased pulse rate, difficulty in reading small print, difficulty in handling small objects and insomnia. Progressively, it is understood that tachycardia may occur, and a slightly unstable person, especially, may suffer marked swings in mood. Physical exercise apparently becomes increasingly fatiguing, and weight loss occurs to spite substantial food intake. When the medication is withdrawn, the adverse reaction usually clears in one week.

The metronidazole treatment described does not appear to damage the hematopoietic or the reticuloendothelial systems.

In the treatment of herpes zoster and herpes simplex, the painful pruritus and vesicular eruptions in most cases markedly subsided approximately forty-eight hours after the beginning of treatment. In the most refractory cases, the patient generally improved in one week on 125 mgs of metronidazole, t.i.d. with a complete clearing of symptoms. This is contrasted with prior treatment of herpes zoster and herpes simplex viral infections which generally have been merely supportive, sometimes utilizing systemic and topical corticosteriods.

Over the past several years metronidazole has been tried with various effectiveness for the treatment of trichomonas vaginalis infections, alcoholism, ameobic dysentery, ameobic liver abscess, leishmaniasis and giardia infestations, acute ulcerative gingivitis, long standing indolent ischemic ulcers found in peripheral vascular disease, scleroderma, schizphrenia and in diabetic retinopathy, but apparently its effectiveness in viral infections has not been heretofore known.

Because considerable suspicion exists that infectious mononucleosis is usually associated with a primary infection of herpes-type virus, metronidazole is indicated as a likely candidate for treating infectious mononucleosis. Likewise, in view of a growing suspicion that virus infection is intimately associated with the development of multiplesclerosis, the treatment described herein would appear to be indicated.

Metronidazole apparently interferes directly with the synthesis of DNA viruses, in a similar manner that occurs with cytosine arabinoside. Metronidazole also apparently interferes with protein synthesis, as uric acid levels increase during therapy and may in some instances manifest itself in acute gout.

It is to be understood that while certain practices of this invention have been described herein, it is not to be limited to the specific form described except insofar as such limitations are included in the following claims.

What I claim and desire to secure by Letters Patent is:

1. A method for treating a human host having a herpes viral infection selected from the group consisting of at least one of the following; zoster, simplex, hominus and mononeucleosis comprising:
   a. repeatedly orally administering anti-herpes viral infection effective amounts of a pharmaceutical composition which contains, as an active ingredient, 1-(β-hydroxyethyl)-2-methyl-5-nitromidazole to a human host in need of said treatment.

2. The method of claim 1 wherein:
   a. the dosage range of the composition in adult human patients is about 31 mgs to 1,000 mgs per 24 hour period.

3. The method of claim 1 wherein:
   a. the dosage amount is substantially reduced following initial administration over a period including a plurality of weeks.

4. The method of claim 1 wherein:
   a. said composition is administered at a dosage of about 125 mgs per 24 hour period.

* * * * *